United States Patent [19]
Kuribayashi et al.

[11] Patent Number: 6,091,503
[45] Date of Patent: Jul. 18, 2000

[54] METHOD FOR DETERMINING MECHANICAL PROPERTY OF RESIN DISCS AND OPTICAL DISCS

[75] Inventors: Isamu Kuribayashi; Hideki Hirata, both of Tokyo, Japan

[73] Assignee: TDK Corporation, Tokyo, Japan

[21] Appl. No.: 09/327,505

[22] Filed: Jun. 8, 1999

[30] Foreign Application Priority Data

Jun. 23, 1998 [JP] Japan .................................. 10-192359

[51] Int. Cl.[7] ............................ G01N 21/84; G01B 11/04
[52] U.S. Cl. ............................ 356/426; 356/385; 356/384
[58] Field of Search ................................ 356/426, 376, 356/377, 384, 372, 237.1, 239.1, 239.2, 239.7, 244, 387; 250/559.19, 559.22, 559.24

[56] References Cited

U.S. PATENT DOCUMENTS

| | | | |
|---|---|---|---|
| 4,639,141 | 1/1987 | Kuwabara et al. | 356/387 |
| 4,652,738 | 3/1987 | Nishihara et al. | 250/202 |
| 4,887,904 | 12/1989 | Nakazato et al. | 356/375 |
| 5,194,743 | 3/1993 | Aoyama et al. | 250/548 |
| 5,350,899 | 9/1994 | Ishikawa et al. | 219/494 |
| 5,546,179 | 8/1996 | Cheng | 356/73 |
| 5,940,174 | 8/1999 | Mueller et al. | 356/237.2 |
| 5,983,167 | 11/1999 | Ebisawa | 702/167 |
| 5,986,753 | 11/1999 | Seelig et al. | 356/244 |

FOREIGN PATENT DOCUMENTS 7-52512  6/1995  Japan .

*Primary Examiner*—Frank G. Font
*Assistant Examiner*—Michael P. Stafira
*Attorney, Agent, or Firm*—Oblon, Spivak, McClelland, Maier & Neustadt, P.C.

[57] ABSTRACT

A mechanical property such as axial acceleration of an injection molded resin disc substrate or an optical disc comprising the same is determined by measuring a variation in radius or diameter of the substrate or disc in its circumferential direction, and determining the mechanical property of the substrate or disc from the measurement.

3 Claims, 1 Drawing Sheet

METHOD FOR DETERMINING MECHANICAL PROPERTY OF RESIN DISCS AND OPTICAL DISCS

BACKGROUND OF THE INVENTION

Optical discs must have sufficient mechanical properties to ensure reliable writing and reading operation. Optical discs using injection molded resin disc substrates, however, are difficult to fabricate to consistent mechanical properties. It is often necessary to measure mechanical properties of such discs.

Among mechanical properties of optical discs, the axial runout of an optical disc during rotation is generally measured using an instrument having an optical head. Since focus control is made such that an objective built in the optical head may follow the disc surface, this instrument determines an axial runout and an axial acceleration by measuring the travel distance of the objective. The travel of the object can be determined from a change of the capacitance between a stationary electrode and a movable electrode attached to the objective (see JP-B 7-52512). The instrument utilizing this principle is marketed, for example, as optical disc mechanical precision instrument model ODA-II by Shin-Denshi Kogyo K. K. and optical disc mechanical property instrument LM series by Ono Sokki K. K.

The above-described prior art instruments carry out measurement by causing the objective of the optical head to follow the axial runout of a disc during rotation, determining the travel of the objective, and calculating an axial runout or axial acceleration from the travel. This procedure ensures a high precision of measurement, but takes a long time of the order of minute from the start of measurement to the end of calculation. If a whole number of discs are to be inspected in the manufacturing line, a plurality of instruments must be installed to compensate for a drop of productivity. However, since the instruments are expensive, it is practically very difficult to inspect a whole number of discs.

SUMMARY OF THE INVENTION

An object of the invention is to provide a method for determining a mechanical property of resin discs for used as optical disc substrates as well as a mechanical property of optical discs having resin disc substrates, using simple means.

According to the invention, there is provided a method for determining a mechanical property of an injection molded resin disc, comprising the steps of measuring a variation in radius or diameter of the disc in its circumferential direction, and determining the mechanical property of the disc from the measured variation. The resin disc is typically a substrate for an optical disc.

In another aspect, the invention provides a method for determining a mechanical property of an optical disc comprising an injection molded resin disc substrate, comprising the steps of measuring a variation in radius or diameter of the optical disc in a circumferential direction, and determining the mechanical property of the optical disc from the measured variation.

DETAILED DESCRIPTION OF THE INVENTION

Figure 1:
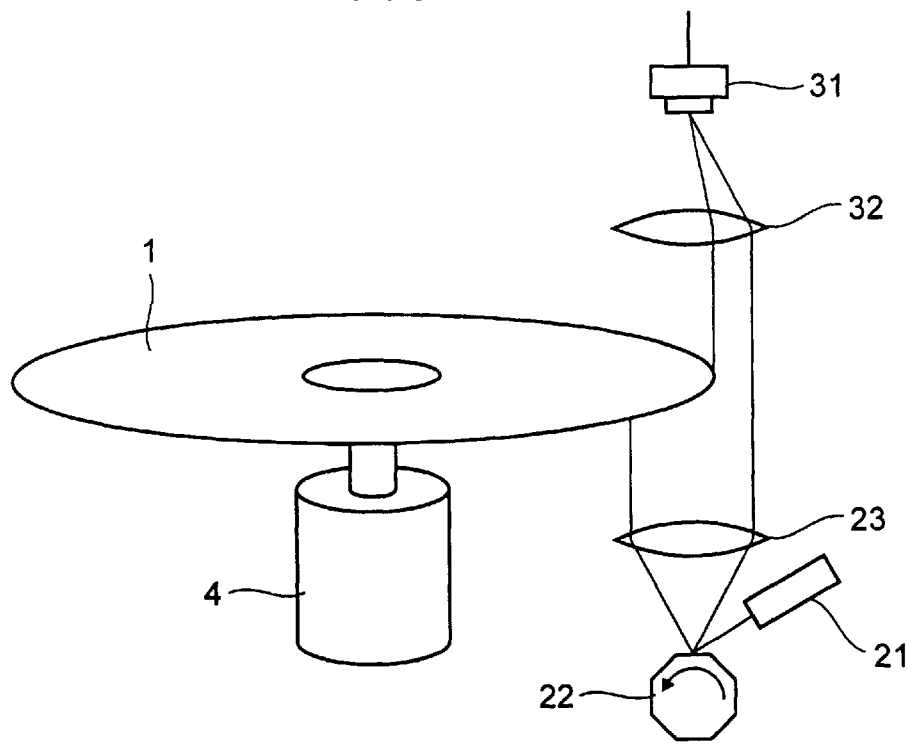
FIG. 1 schematically illustrates a system for measuring a variation in radius of a disc according to the method of the invention.

In general, the mechanical property of a resin disc becomes worst at the innermost and outermost peripheries of the disc. This is because resin discs are formed by injection molding resin material in a mold. There is a tendency that strains are introduced at the innermost periphery where the molten resin flows out and at the outermost periphery where the resin stops.

Disc substrates for optical discs are known as one application where resin discs having an excellent mechanical property are required. The drives for optical discs include drives of the CAV mode of controlling the angular velocity (or number of revolutions) constant and drives of the CLV mode of controlling the linear velocity constant. In the CAV mode wherein the disc rotates at a constant number of revolutions, the linear velocity is highest at the outermost periphery. Then, the mechanical property of the innermost periphery with a slower linear velocity does have little influence on the reliability of writing and reading operation, but the mechanical property of the outermost periphery has a substantial influence on the reliability. On the other hand, in the CLV mode wherein the disc rotates at a constant linear velocity, the influence of mechanical property is equal between the innermost and outermost peripheries. Nevertheless, in most actual discs, the outermost periphery has a poorer mechanical property than the innermost periphery. Therefore, in the CLV mode too, it is mainly the mechanical property of the outermost periphery that governs the reliability of discs.

We have found that the mechanical property of an injection molded resin disc at its outer periphery is correlated to a variation in radius or diameter of the disc in its circumferential direction, and that when the variation in radius or diameter of a disc in its circumferential direction is large, the axial acceleration of the disc is also high. A close linear correlation is found between the variation in radius or diameter and the axial acceleration while this correlation differs with the material and dimensions (e.g., diameter and thickness) of the disc. If the correlation or calibration is previously empirically established for a particular type of disc or a manufacturing lot, then the mechanical property of a disc can be known by measuring only the variation of the radius or diameter. Disc samples can be readily inspected whether or not they are rejected.

The instrument for measuring a variation in radius or diameter of the disc in a circumferential direction, that is, the difference between a maximum radius and a minimum radius of the disc or the difference between a maximum diameter and a minimum diameter of the disc is not critical although an optical instrument capable of non-contact high-speed measurement is preferable. For example, a conventional instrument commercially available as a laser scanning micrometer from Mitutoyo K. K. may be modified into an instrument with which the method of the invention can be carried out.

FIG. 1 illustrates a measuring system utilizing the construction of a main section of the laser scanning micrometer. The instrument includes a light-emitting unit 21 having a laser diode for emitting a laser beam and a light-receiving unit 31 for receiving the laser beam. Disposed between these units are a rotating polygon mirror 22 for reflecting the laser beam from the light-emitting unit 21 into a sector shape, a collimator lens 23 for converting the sector shaped laser beams into parallel scanning laser beams, and a condenser lens 32 for collecting the parallel scanning laser beams at the light-receiving unit 31. The system further includes a motor 4 as means for rotating a disc 1.

Using the instrument, a variation in radius of the disc 1 in its circumferential direction is measured as follows. First of all, the disc 1 is placed between the light emitting and receiving units 21 and 31 such that the outer periphery of the disc 1 may be positioned within the region where laser beams travel in parallel. Differently stated, the disc 1 is placed such that parallel scanning laser beams may be intercepted by the disc 1 for a duration, but not intercepted by the disc 1 for the remaining duration of one scanning cycle. While the motor 4 is driven to rotate the disc 1, the disc 1 is scanned with the laser beam. If the disc 1 has a variation of radius (distance from the axis of rotation to the outer periphery) in the circumferential direction, the duration of time during which the laser beam is intercepted by the disc 1 changes. The light-receiving unit 31 detects a change of the light intercepted duration, thereby measuring the variation in radius of the disc in the circumferential direction. More illustratively, the variation in radius of the disc 1 can be accurately measured by rotating the polygon mirror 22 in synchronization with clock pulses, and counting the number of clock pulses generated within the time duration when the output voltage of the light-receiving unit 31 is reduced. Therefore, the instrument can measure the variation in radius of the disc 1 at a high precision while the instrument is cost effective in design and manufacture.

Preferably the disc surface is perpendicular to the laser beams during measurement. Even when the disc surface is not perpendicular to the laser beams during measurement, the variation in radius of the disc 1 can be accurately determined by performing an appropriate correction.

When a variation in diameter of a disc is to be measured, two optical instruments are arranged at diametrically opposite sides of the disc. The measurement of a variation in diameter of a disc can cancel any misalignment of the disc mounted in the instrument.

In the illustrated instrument, the number of revolutions of the disc during measurement is not critical. With this instrument, measurement is complete when the disc has made one turn. Then, even when the disc is rotated at a relatively low speed, for example, at about 60 rpm, the measurement is complete within a sufficiently short time in the practically acceptable range. Therefore, the number of revolutions of the disc is appropriately set in the range within which the motor 4 can rotate at a constant speed without shaft vibration or other undesirable problems.

The articles to which the invention is applicable include resin discs and optical discs having resin disc substrates, for example, read only optical discs such as CD-ROM and DVD-ROM, and optical recording discs having such recording layers as dye base recording layers, phase change type recording layers or magneto-optical recording layers. The invention works whether the optical disc is of the single substrate type or of the dual substrate type (or laminate type). As opposed to the prior art mechanical property measuring systems, the system of the invention is capable of measurement on a bare disc on which the recording layer or reflective layer that reflects the measuring light beam has not been formed, that is, on a resin disc substrate alone. Therefore, the quality as a product (optical disc) can be determined before the recording layer and reflective layer are formed thereon. The invention is advantageously applicable to those resin discs which are otherwise difficult to determine a mechanical property, for example, thin resin disc substrates (thickness 0.6 mm or less) for use in high-density recording optical discs such as DVD, and optical discs having such thin resin disc substrates.

EXAMPLE

Disc substrate samples having a diameter of 120 mm and a thickness of 0.6 mm, designated sample Nos. 1, 2 and 3, were prepared from polycarbonate by injection molding. In preparing these samples, the resin was molded under different conditions, that is, at different mold temperatures.

Using an optical disc mechanical precision instrument model ODA-II by Shin-Denshi Kogyo K. K., each disc sample was measured for instantaneous axial acceleration at a position of radius 55 mm while rotating the disc sample at 1,800 rpm. The time required for this measurement was about 2 minutes.

Next, the measuring system constructed as in FIG. 1 was fabricated utilizing the laser scanning micrometer from Mitutoyo K. K. While the motor 4 was driven to rotate the disc sample at 60 rpm, laser beams were irradiated to the disc for measuring a variation in radius of the disc sample in its circumferential direction. The time required for this measurement was about 10 seconds.

Figure 2:
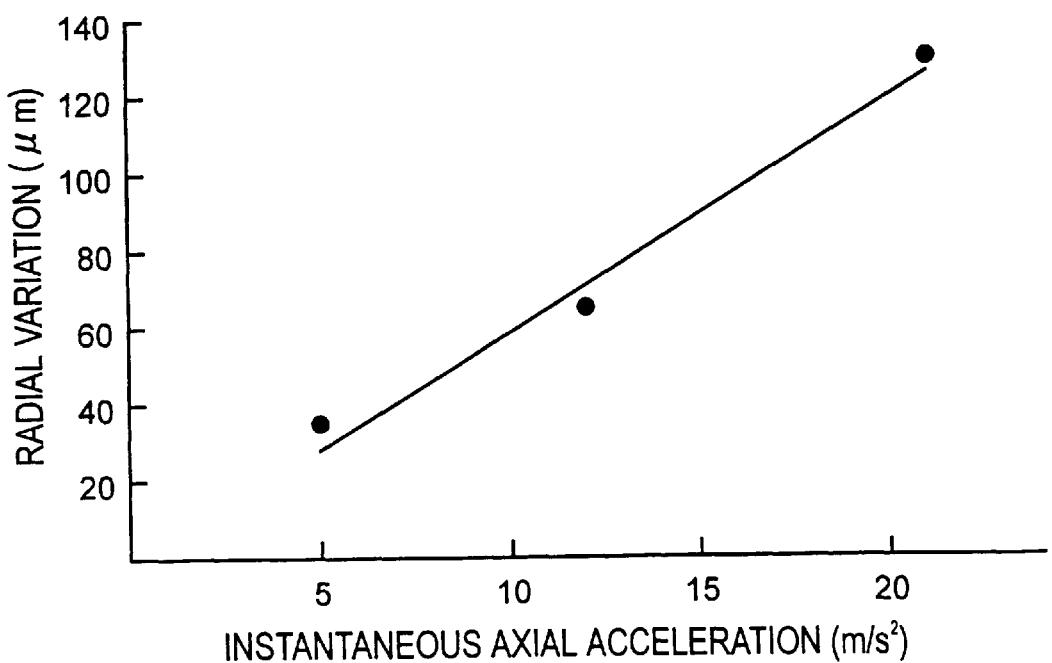
FIG. 2 is a graph showing the axial acceleration versus the radial variation of resin discs.

The axial acceleration and radial variation of the samples are shown in Table 1 and plotted in FIG. 2.

TABLE 1

| Sample No. | Instantaneous axial acceleration $(m/s^2)$ | Radial variation $(\mu m)$ |
|---|---|---|
| 1 | 21 | 130 |
| 2 | 12 | 65 |
| 3 | 5 | 35 |

As seen from FIG. 2, a close linear correlation exists between axial acceleration and radial variation. This indicates that the axial acceleration can be correctly presumed from the radial variation.

Using a measuring system which takes a substantially shorter time for measurement and is manufactured at a lower cost than the conventional axial acceleration measuring system, the invention can determine the mechanical property of resin discs and optical discs. If the invention is utilized in the inspection step in the optical disc manufacturing process, the invention is effective for minimizing a productivity drop and a cost increase associated with the inspection step. The invention permits a whole number of samples to be inspected.

Japanese Patent Application No. 192359/1998 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A method for determining a mechanical property of an injection molded resin disc, comprising the steps of:

measuring a variation in radius or diameter of the disc in its circumferential direction, and determining the mechanical property of the disc from the measured variation.

2. The method of claim 1 wherein said resin disc is a substrate for an optical disc.

3. A method for determining a mechanical property of an optical disc comprising an injection molded resin disc substrate, comprising the steps of:

measuring a variation in radius or diameter of the optical disc in a circumferential direction, and determining the mechanical property of the optical disc from the measured variation.

* * * * *